United States Patent
Crowley et al.

(10) Patent No.: US 10,426,555 B2
(45) Date of Patent: Oct. 1, 2019

(54) MEDICAL INSTRUMENT WITH SENSOR FOR USE IN A SYSTEM AND METHOD FOR ELECTROMAGNETIC NAVIGATION

(71) Applicant: COVIDIEN LP, Mansfield, MA (US)

(72) Inventors: Thomas P. Crowley, Lino Lakes, MN (US); David J. Miel, Minneapolis, MN (US); David J. Serdar, Shorewood, MN (US); Joshua B. Stopek, Minneapolis, MN (US); David M. Costello, Delano, MN (US); Lev A. Koyrakh, Plymouth, MN (US); Keith E. Jasperson, Andover, MN (US); Jon D. Schell, Shoreview, MN (US)

(73) Assignee: COVIDIEN LP, Mansfield, MA (US)

( * ) Notice: Subject to any disclaimer, the term of this patent is extended or adjusted under 35 U.S.C. 154(b) by 578 days.

(21) Appl. No.: 15/147,273

(22) Filed: May 5, 2016

(65) Prior Publication Data
US 2016/0354160 A1     Dec. 8, 2016

Related U.S. Application Data

(60) Provisional application No. 62/170,383, filed on Jun. 3, 2015.

(51) Int. Cl.
*A61B 5/00* (2006.01)
*A61B 34/20* (2016.01)
(Continued)

(52) U.S. Cl.
CPC ............ *A61B 34/20* (2016.02); *A61B 1/2676* (2013.01); *A61B 5/0071* (2013.01); *A61B 5/055* (2013.01);
(Continued)

(58) Field of Classification Search
None
See application file for complete search history.

(56) References Cited

U.S. PATENT DOCUMENTS

| 1,576,781 A | 3/1926 | Phillips |
| 1,735,726 A | 11/1929 | Bornhardt |

(Continued)

FOREIGN PATENT DOCUMENTS

| CA | 964149 | 3/1975 |
| DE | 3042343 A1 | 6/1982 |

(Continued)

OTHER PUBLICATIONS

McKenna, N.J. et al., "Nuclear Receptor Coregulators: Cellular and Molecular Biology," Endocrine Reviews 20(3): 321-344, Jun. 1, 1999, 24 pages.

(Continued)

*Primary Examiner* — Ronald Laneau

(57) ABSTRACT

A medical instrument includes a printed sensor, a surface, at least one non-conductive material, and at least one pair of contacts. The sensor has at least one coil formed on a conductive material. The surface is suitable for receiving the printed sensor and can be placed in an EM field. The at least one non-conductive material covers the at least one coil of the sensor. The medical instrument contains multiple conductive and nonconductive layers. The at least one pair of contacts are electrically connected to the at least one coil and connectable to the conductive layer, the conductive layer coupled to a measurement device, which senses an induced electrical signal based on a magnetic flux change of the EM field. The location of the medical instrument in a coordinate system of the EM filed is identified based on the induced electrical signal in the sensor.

20 Claims, 10 Drawing Sheets

(51) Int. Cl.

| | | |
|---|---|---|
| *A61M 25/01* | (2006.01) | |
| *A61B 10/06* | (2006.01) | |
| *A61B 10/02* | (2006.01) | |
| *A61B 5/055* | (2006.01) | |
| *A61B 1/267* | (2006.01) | |
| *A61B 34/10* | (2016.01) | |
| *A61B 5/06* | (2006.01) | |
| *A61B 10/04* | (2006.01) | |
| *A61B 17/00* | (2006.01) | |

(52) U.S. Cl.
CPC .......... *A61B 5/062* (2013.01); *A61B 10/0233* (2013.01); *A61B 10/04* (2013.01); *A61B 10/06* (2013.01); *A61B 34/10* (2016.02); *A61M 25/0105* (2013.01); *A61B 2010/0216* (2013.01); *A61B 2017/00526* (2013.01); *A61B 2017/00699* (2013.01); *A61B 2017/00849* (2013.01); *A61B 2017/00853* (2013.01); *A61B 2017/00929* (2013.01); *A61B 2034/105* (2016.02); *A61B 2034/107* (2016.02); *A61B 2034/2051* (2016.02); *A61M 2025/0166* (2013.01)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |

(56) References Cited

U.S. PATENT DOCUMENTS

| | | |
|---|---|---|
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |

(56) References Cited

U.S. PATENT DOCUMENTS

| | | |
|---|---|---|
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,700,236 A | 12/1997 | Sauer et al. |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Natis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |

(56) References Cited

U.S. PATENT DOCUMENTS

| | | |
|---|---|---|
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |

(56) References Cited

U.S. PATENT DOCUMENTS

| | | | |
|---|---|---|---|
| 6,551,325 B2 | 4/2003 | Neubauer et al. |
| 6,580,938 B1 | 6/2003 | Acker |
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |
| 6,846,286 B2 | 1/2005 | Suzuki et al. |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Yokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,998,062 B2 | 8/2011 | Gilboa |
| 8,190,238 B2 | 5/2012 | Moll et al. |
| 8,828,201 B2 * | 9/2014 | Simpson ............ A61B 5/14532 |
| | | 204/403.01 |
| 8,932,207 B2 | 1/2015 | Greenburg et al. |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0026097 A1 | 2/2002 | Akiba |
| 2002/0067408 A1 | 6/2002 | Adair et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0028096 A1 | 2/2003 | Niwa et al. |
| 2003/0040657 A1 | 2/2003 | Yamaya et al. |
| 2003/0074011 A1 | 4/2003 | Gilboa et al. |
| 2003/0086599 A1 | 5/2003 | Armato et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller |
| 2005/0022993 A1 | 2/2005 | Wilson et al. |
| 2005/0033149 A1 | 2/2005 | Strommer et al. |
| 2005/0075680 A1 * | 4/2005 | Lowry ................ A61N 1/0531 |
| | | 607/45 |
| 2005/0080342 A1 | 4/2005 | Gilreath et al. |
| 2005/0085715 A1 | 4/2005 | Dukesherer et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2005/0229934 A1 | 10/2005 | Willeford |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon et al. |
| 2006/0149134 A1 | 7/2006 | Soper et al. |
| 2007/0015964 A1 | 1/2007 | Eversull et al. |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0197896 A1 | 8/2007 | Moll et al. |
| 2007/0225559 A1 | 9/2007 | Clerc et al. |
| 2007/0265639 A1 | 11/2007 | Danek et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |

(56) References Cited

U.S. PATENT DOCUMENTS

| | | |
|---|---|---|
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |
| 2009/0234223 A1 | 9/2009 | Onoda et al. |
| 2010/0016757 A1 | 1/2010 | Greenburg et al. |
| 2011/0207997 A1 | 8/2011 | Greenburg et al. |
| 2012/0150022 A1 | 6/2012 | Bar-Tal et al. |
| 2013/0066194 A1* | 3/2013 | Seter .............. A61B 5/062 600/424 |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19610984 A1 | 9/1997 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0651968 A1 | 5/1995 |
| EP | 0796633 A1 | 9/1997 |
| EP | 0857461 A2 | 8/1998 |
| EP | 0894473 A2 | 2/1999 |
| EP | 0908146 A2 | 4/1999 |
| EP | 0 922 966 A2 | 6/1999 |
| EP | 0930046 A2 | 7/1999 |
| EP | 1078644 A1 | 2/2001 |
| EP | 1255113 A1 | 11/2002 |
| EP | 2096523 A1 | 9/2009 |
| EP | 2755554 A1 | 7/2014 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | 06194639 A | 7/1994 |
| JP | 07-043619 A | 2/1995 |
| JP | 10-197807 A | 7/1998 |
| JP | 2000-075218 A | 3/2000 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 9605768 A1 | 2/1996 |
| WO | 96/11624 A2 | 4/1996 |
| WO | 96/32059 A1 | 10/1996 |
| WO | 97/29682 A1 | 8/1997 |
| WO | 97/29684 A1 | 8/1997 |
| WO | 97/36192 A1 | 10/1997 |
| WO | 97/49453 A1 | 12/1997 |
| WO | 98/08554 A1 | 3/1998 |
| WO | 98/38908 A1 | 9/1998 |
| WO | 99/15097 A2 | 4/1999 |
| WO | 99/21498 A1 | 5/1999 |
| WO | 99/23956 A1 | 5/1999 |
| WO | 99/26549 A1 | 6/1999 |
| WO | 99/27839 A2 | 6/1999 |
| WO | 99/29253 A1 | 6/1999 |
| WO | 99/32033 A1 | 7/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 99/60939 A1 | 12/1999 |
| WO | 00/06701 A1 | 2/2000 |
| WO | 00/10456 A1 | 3/2000 |
| WO | 00/16684 A1 | 3/2000 |
| WO | 00/35531 A1 | 6/2000 |
| WO | 01/30437 A1 | 5/2001 |
| WO | 01/67035 A1 | 9/2001 |
| WO | 01/87136 A2 | 11/2001 |
| WO | 01/87398 A2 | 11/2001 |
| WO | 01/91842 A1 | 12/2001 |
| WO | 02/24054 A2 | 3/2002 |
| WO | 02/064011 A2 | 8/2002 |
| WO | 02/070047 A1 | 9/2002 |
| WO | 03/086498 A2 | 10/2003 |
| WO | 2004/023986 A1 | 3/2004 |
| WO | 2005025635 A2 | 3/2005 |
| WO | 2007033379 A2 | 3/2007 |
| WO | 2013/038354 A1 | 3/2013 |
| WO | 2013/056006 A2 | 4/2013 |
| WO | 2013/98715 A1 | 7/2013 |
| WO | 2014/061354 A1 | 4/2014 |
| WO | 2015116687 A1 | 8/2015 |

OTHER PUBLICATIONS

Ding, X.F. et al., "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities," Molecular Endocrinology12:302-313, Feb. 1, 1998 (9 pages).

Stenoien, D.L. et al., "Ligand-Mediated Assembly and Real-Time Cellular Dynamics of Estrogen Receptor .alpha.-Coactivator Complexes in Living Cells," Molecular and Cellular Biology, Jul. 2001, pp. 4404-4412, 9 pages.

International Search Report and Written Opinion from Appl. No. PCT/US2016/033063 dated Aug. 16, 2016.

Chinese Office Action dated Jan. 7, 2019 issued in corresponding CN Appln. No. 2016800320825. (Summary only).

Extended European Search Report issued in corresponding Appl. No. EP 16803978.2 dated Feb. 21, 2019 (8 pages).

* cited by examiner

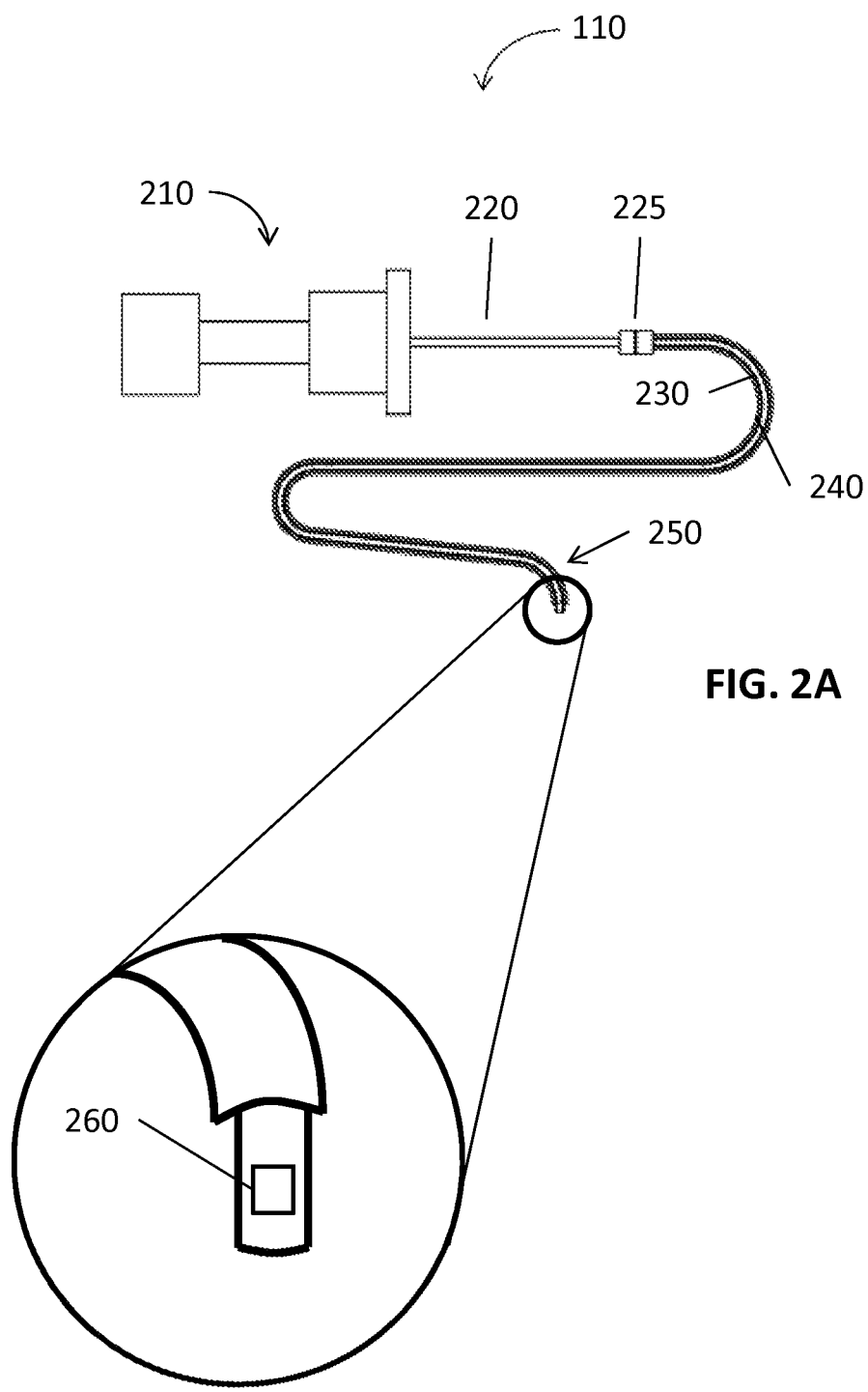

MEDICAL INSTRUMENT WITH SENSOR FOR USE IN A SYSTEM AND METHOD FOR ELECTROMAGNETIC NAVIGATION

CROSS REFERENCE TO RELATED APPLICATION

The present application claims the benefit of and priority to U.S. Provisional Application Ser. No. 62/170,383, filed on Jun. 3, 2015, the entire contents of which are incorporated herein by reference.

BACKGROUND

Technical Field

The present disclosure relates to a medical instrument including a sensor, and a system in which the location of the sensor can be detected and tracked. More particularly, the present disclosure relates to systems and methods that identify a location of a medical instrument having the sensor in an electromagnetic field.

Discussion of Related Art

Electromagnetic navigation (EMN) has helped expand the possibilities of treatment to internal organs and diagnosis of diseases. EMN relies on non-invasive imaging technologies, such as computed tomography (CT) scanning, magnetic resonance imaging (MRI), or fluoroscopic technologies. These images may be registered to a location of a patient within a generated magnetic field, and as a result the location of a sensor placed in that field can be identified with reference to the images. As a result, EMN in combination with these non-invasive imaging technologies is used to identify a location of a target and to help clinicians navigate inside of the patient's body to the target.

In one particular example of currently marketed systems in the area of locating the position of medical instruments in a patient's airway, a sensor is placed at the end of a probe referred to as a locatable guide and passed through an extended working channel (EWC) or catheter, and the combination is inserted into the working channel of a bronchoscope. The EWC and probe with sensor is then navigated to the target within the patient. Once the target is reached, the locatable guide (i.e., sensor and probe) can be removed and one or more instruments, including biopsy needles, biopsy brushes, ablation catheters, and the like can be passed through the working channel and EWC to obtain samples and/or treat the target. At this point, however, because the locatable guide with its sensor have been removed, the exact location of a distal end of the EWC, and by extension any instrument which might be passed there through is not precisely known.

Images generated by the non-invasive imaging technologies described above do not provide the resolution of live video imaging. To achieve live video, a clinician may utilize the features of an endoscope. However, an endoscope is limited by its size and as a result cannot be navigated to the pleura boundaries of the lungs and other very narrow passageways as is possible with tools typically utilized in EMN. An alternative is a visualization instrument that is inserted through the EWC and working channel of the endoscope, which can be sized to reach areas such as the pleura boundaries.

As with the locatable guide, however, once the visualization instrument is removed the location of the distal end of the EWC is unclear. One technique that is used is the placement of one or more markers into the tissue near the target and the use of fluoroscopy to confirm location of the EWC and the markers, and any subsequent instruments passed through the EWC. Due to the small diameter of the EWC, simultaneous insertion of more than one instrument may be impractical. Thus, repeated insertions and removals of instruments for visualization, diagnosis, and surgeries are necessitated. Such repeated insertions and removals lengthen diagnostic or surgical time and efforts, and increase costs on patients correspondingly. Thus, it is desirous to make a fewer insertion and/or removal of instruments to shorten times necessary for diagnosis and surgeries while at the same time increasing the certainty of the location of the EWC and instruments passed through the EWC, including imaging modalities.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Provided in accordance with the present disclosure is a medical instrument having a distal portion and a proximal portion, the medical instrument comprising a sensor printed on a distal portion of the medical instrument and having at least one coil formed of a conductive material, at least one non-conductive material covering the at least one coil of the at least one sensor, a conductive layer printed circumferentially around the proximal portion of the medical instrument, a nonconductive layer printed on top of the conductive layer, and at least one pair of contacts electrically connected to the at least one coil and coupled to the conductive layer, the conductive layer connectable to a measurement device configured to sense an induced electrical signal based on a magnetic flux change of the electromagnetic field, wherein a location of the medical instrument in a coordinate system of the electromagnetic field is identified based on the induced electrical signal in the sensor.

According to aspects of the disclosure, the medical instrument comprises a base non-conductive layer on the distal portion of the medical instrument on which the conductive material is printed. The sensor may include multiple layers of the conductive material and the non-conductive material printed or fabricated on the distal portion of the medical instrument. Each conductive layer may have a different configuration, including a different pitch angle and/or the number of loops of the conductive material.

According to further aspects of the disclosure, the proximal portion of the medical instrument includes a plurality of conductive layers and non-conductive layers printed on the proximal portion of the medical instrument. Each conductive layer is coupled to one of the conductive materials of the sensor. The conductive material may further be connected to the conductive layer through vias. The conductive material may further form a helical shape which may be formed in a counter-clockwise or clockwise direction. In embodiments, the outer surface of the medical instrument is made of ETFE, PTFE, polyimide, or non-conductive polymer. The conductive materials may be copper, silver, gold, conductive alloys, or a conductive polymer. The medical instrument may be an extended working channel, an imaging instrument, a biopsy forceps, a biopsy brush, a biopsy needle, or a microwave ablation probe.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which:

FIG. 2A is a profile view of a catheter guide assembly and medical instrument in accordance with an embodiment of the present disclosure;

FIG. 2B is an enlarged view of the indicated area of detail of FIG. 2A;

DETAILED DESCRIPTION

The present disclosure is related to medical instruments, systems and methods for identifying a location of medical instruments in an electromagnetic field by using a sensor. The sensors may be printed directly on or separately fabricated and then affixed to the medical instruments, including imaging instruments. Since the sensor may be inserted inside of patient's body with medical instruments, the location of the medical instruments is identified in real-time. Further, the sensor may provide and trace an exact direction and location of the medical instrument with other imaging modalities. Due to the small size of the sensor, medical instruments may incorporate the sensor inside or outside of the medical instruments, to facilitate continuous navigation. Although the present disclosure will be described in terms of specific illustrative embodiments, it will be readily apparent to those skilled in this art that various modifications, rearrangements, and substitutions may be made without departing from the spirit of the present disclosure. The scope of the present disclosure is defined by the claims appended to this disclosure.

Figure 1:
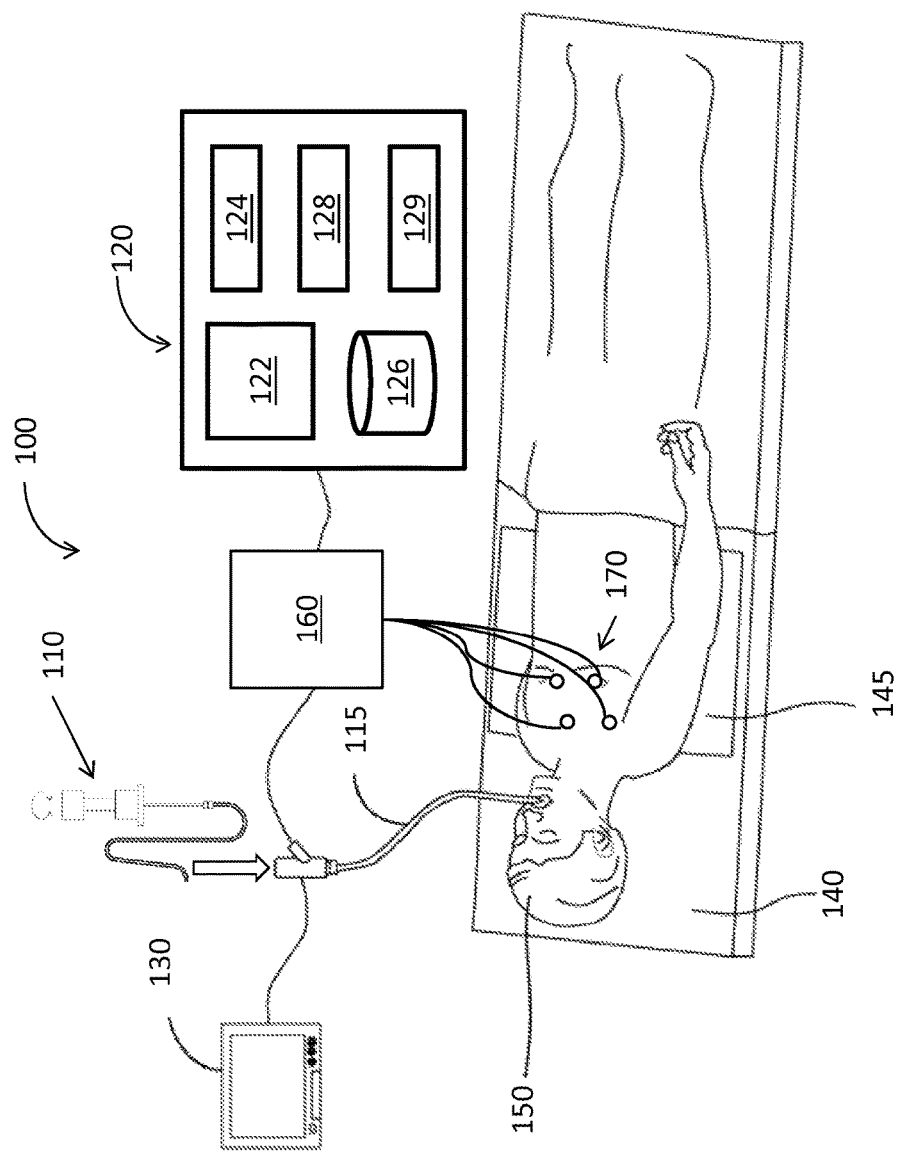
FIG. 1 is a perspective view of a system for identifying a location of a medical instrument in accordance with an embodiment of the present disclosure.

FIG. 1 illustrates one illustrative embodiment of a system and method for identifying a location of medical instruments in an electromagnetic field. In particular, an electromagnetic navigation (EMN) system 100, which is configured to utilize CT, MRI, or fluoroscopic images, is shown. One such EMN system may be the ELECTROMAGNETIC NAVIGATION BRONCHOSCOPY® system currently sold by Covidien LP. The EMN system 100 includes a catheter guide assembly 110, a bronchoscope 115, a computing device 120, a monitoring device 130, an EM board 140, a tracking device 160, and reference sensors 170. The bronchoscope 115 is operatively coupled to the computing device 120 and the monitoring device 130 via a wired connection (as shown in FIG. 1) or wireless connection (not shown).

FIG. 2A illustrates an embodiment of the catheter guide assembly 110 of FIG. 1. The catheter guide assembly 110 includes a control handle 210, which enables advancement and steering of the distal end 250 of the catheter guide assembly 110. The catheter guide assembly 110 includes a locatable guide catheter (LG) 220 inserted in the EWC 230 and an electromagnetic (EM) sensor 260, as shown in FIG. 2B. A locking mechanism 225 secures the EWC 230 and the LG 220 to one another. Catheter guide assemblies usable with the instant disclosure may be currently marketed and sold by Covidien LP under the name SUPERDIMENSION® Procedure Kits and EDGE™ Procedure Kits. For a more detailed description of the catheter guide assemblies, reference is made to commonly-owned U.S. patent application Ser. No. 13/836,203 filed on Mar. 15, 2013, by Ladtkow et al. and U.S. Pat. No. 7,233,820, the entire contents of which are incorporated in this disclosure by reference. As will be described in greater detail below, the EM sensor 260 on the distal portion of the LG 220 senses the electromagnetic field, and is used to identify the location of the LG 220 in the electromagnetic field. In embodiments, the EM sensor 260 can be directly integrated into the distal end of the EWC 230.

In use, the bronchoscope 115 is inserted into the mouth or through an incision of a patient 150 to capture images of the internal organ. In the EMN system 100, inserted into the bronchoscope 115 is a catheter guide assembly 110 for achieving an access to the internal organ of the patient 150. The catheter guide assembly 110 may include an extended working channel (EWC) 230 into which a locatable guide catheter (LG) 220 with the EM sensor 260 at the distal portion is inserted. The EWC 230, the LG 220, and the EM sensor 260 are used to navigate through the internal organ as described in greater detail below.

In an alternative embodiment, instead of a bronchoscope 115 inserted via a natural orifice the catheter guide assembly 110 is inserted into the patient 150 via an incision. The catheter guide assembly 110 including the EWC 230 may be inserted through the incision to navigate a luminal network other than the airways of a lung, such as the cardiac luminal network.

The computing device 120, such as, a laptop, desktop, tablet, or other similar computing device, includes a display 122, one or more processors 124, memory 126, a network card 128, and an input device 129. The EMN system 100 may also include multiple computing devices, wherein the separate computing devices are employed for planning, treatment, visualization, and other aspects of assisting clinicians in a manner suitable for medical operations. The display 122 may be touch-sensitive and/or voice-activated, enabling the display 122 to serve as both input and output devices. The display 122 may display two dimensional (2D) images or a three dimensional (3D) model of an internal organ, such as the lung, prostate, kidney, colon, liver, etc., to locate and identify a portion of the internal organ that displays symptoms of diseases.

The display 122 may further display options to select, add, and remove a target to be treated and settable items for the visualization of the internal organ. In an aspect, the display 122 may also display the location of the catheter guide assembly 110 in the electromagnetic field based on the 2D images or 3D model of the internal organ.

The one or more processors 124 execute computer-executable instructions. The processors 124 may perform image-processing functions so that the 3D model of the internal organ can be displayed on the display 122. In embodiments, the computing device 120 may further include a separate graphic accelerator (not shown) that performs only the image-processing functions so that the one or more processors 124 may be available for other programs. The memory 126 stores data and programs. For example, data may be image data for the 3D model or any other related data such as patients' medical records, prescriptions and/or history of the patient's diseases.

One type of programs stored in the memory 126 is a 3D model and pathway planning software module (planning software). An example of the 3D model generation and pathway planning software may be the ILOGIC® planning suite currently sold by Covidien LP. When image data of a patient, which is typically in digital imaging and communications in medicine (DICOM) format, from for example a CT image data set (or an image data set by other imaging modality) is imported into the planning software, a 3D model of the internal organ is generated. In an aspect, imaging may be done by CT imaging, magnetic resonance imaging (MRI), functional MRI, X-ray, and/or any other imaging modalities. To generate the 3D model, the planning software employs segmentation, surface rendering, and/or volume rendering. The planning software then allows for the 3D model to be sliced or manipulated into a number of different views including axial, coronal, and sagittal views that are commonly used to review the original image data. These different views allow the user to review all of the image data and identify potential targets in the images.

Once a target is identified, the software enters into a pathway planning module. The pathway planning module develops a pathway plan to achieve access to the targets and the pathway plan pin-points the location and identifies the coordinates of the target such that they can be arrived at using the EMN system 100, and particularly the catheter guide assembly 110 together with the EWC 230, the LG 220, and the EM sensor 260. The pathway planning module guides a clinician through a series of steps to develop a pathway plan for export and later use during navigation to the target in the patient 150. The term, clinician, may include a doctor, surgeon, nurse, medical assistant, or any user of the pathway planning module involved in planning, performing, monitoring and/or supervising a medical procedure.

Details of these processes and the pathway planning module can be found in U.S. patent application Ser. No. 13/838,805 filed by Covidien LP on Jun. 21, 2013, and entitled "Pathway Planning System and Method," the entire contents of which are incorporated in this disclosure by reference. Such pathway planning modules permit clinicians to view individual slices of the CT image data set and to identify one or more targets. These targets may be, for example, lesions or the location of a nerve which affects the actions of tissue where the disease has rendered the internal organ's function compromised.

The memory 126 may store navigation and procedure software which interfaces with the EMN system 100 to provide guidance to the clinician and provide a representation of the planned pathway on the 3D model and 2D images derived from the 3D model. An example of such navigation software is the ILOGIC® navigation and procedure suite sold by Covidien LP. In practice, the location of the patient 150 in the EM field generated by the EM field generating device 145 must be registered to the 3D model and the 2D images derived from the 3D model. Such registration may be manual or automatic and is described in detail and commonly assigned U.S. Provisional Patent Application 62/020,240 entitled "System and method for navigating within the lung."

As shown in FIG. 1, the EM board 140 is configured to provide a flat surface for the patient to lie down and includes an EM field generating device 145. When the patient 150 lies down on the EM board 140, the EM field generating device 145 generates an EM field sufficient to surround a portion of the patient 150. The EM sensor 260 at the end of the LG 220 is used to determine the location of the distal end of the LG 220 and therewith the EWC 230 within the patient. In an aspect, a separate EM sensor may be located at the distal end of the EWC 230 and therewith the exact location of the EWC 230 in the EM field generated by the EM field generating device 145 can be identified within the patient 150.

Figure 3A:
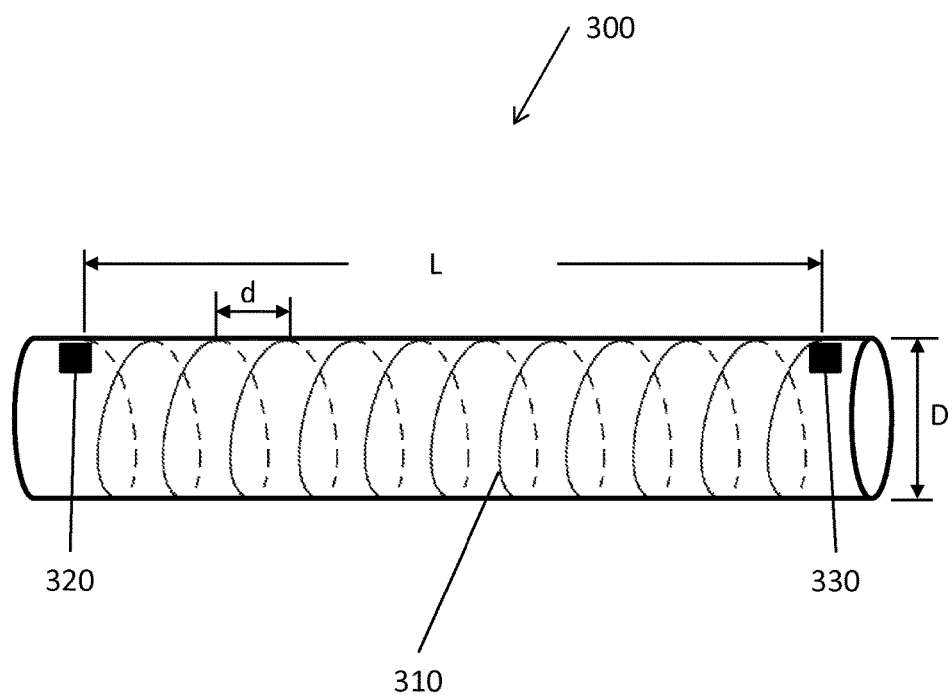
FIG. 3A depicts a sensor as a coil wound and printed at the distal portion of a medical instrument in accordance with an embodiment of the present disclosure.
Figure 3B:
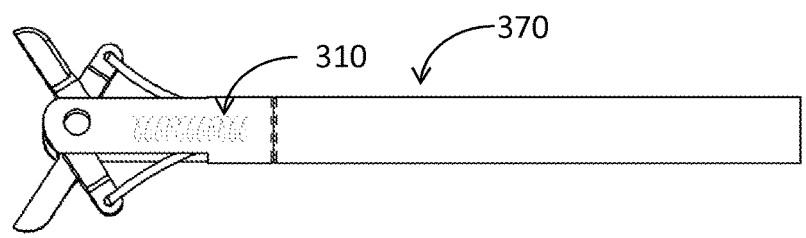
FIGS. 3B-3E are perspective views of a plurality of medical instruments in accordance with an embodiment of the present disclosure.
Figure 3C:
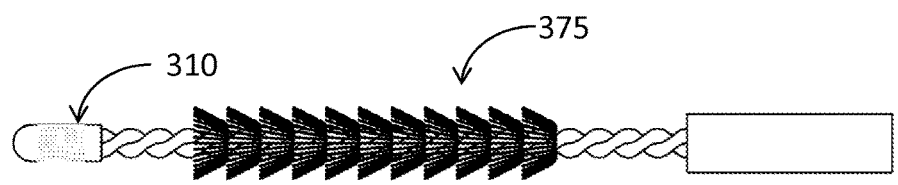
Figure 3D:
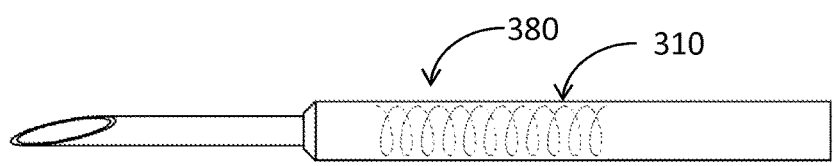
Figure 3E:
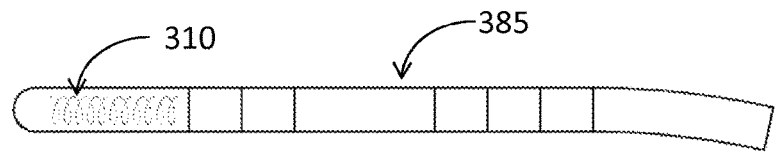

In yet another aspect, the EM board 140 may be configured to be operatively coupled with the reference sensors 170 which are located on the chest of the patient 150. The reference sensors 170 move up following the chest while the patient 150 is inhaling and move down following the chest while the patient 150 is exhaling. The movement of the chest of the patient 150 in the EM field is captured by the reference sensors 170 and transmitted to the tracking device 160 so that the breathing pattern of the patient 150 may be recognized. The tracking device 160 also receives the output of the EM sensor 260, combines both outputs, and compensates the breathing pattern for the location of the EM sensor 260. In this way, the location identified by the EM sensor 260 may be compensated for such that the compensated location of the EM sensor 260 may be synchronized with the 3D model of the internal organ. As noted above, however, the use of an LG 230 with an EM sensor 260 at its distal end 250 can result in challenges surrounding instrument swaps, loss of location information, and a general prolongation of the time needed for a procedure. To alleviate these issues, FIG. 3A depicts an electromagnetic sensor 310 in the shape of a coil. The sensor 310 may be printed directly on the distal portion of a medical instrument 300. The printed electromagnetic sensor (PES) 310 may form a helical shape, as depicted or in another configuration as required by the application. The instrument 300 may be the EWC 230, a catheter, a biopsy instrument, an ablation instrument, a monopolar or bipolar electrosurgical instrument, an imaging instrument, a marking instrument, or a needle, in short any instrument capable of being inserted into the luminal network (e.g., the airways or vasculature of a patient). In one embodiment the instrument 300 is sized to pass through the EWC 230. Alternatively, the instrument 300 may be the EWC 230, as described in more detail below. Other exemplary instruments are shown in FIGS. 3B-3E, depicting biopsy forceps 370, a biopsy brush 375, a biopsy needle 380, and a microwave ablation probe 385, each having an EM sensor 310 applied by the methods of the present disclosure.

As will be described in greater detail below, the distal portion of the instrument 300 may be made of or covered by Ethylene tetrafluoroethylene (ETFE), Polytetrafluoroethylene (PTFE), polyimide, or another suitable material to form a non-conductive base for the sensor 310. If the distal portion of the instrument 300 is not covered or made of a non-conductive material, a non-conductive material must be applied to the distal portion first to form an insulating base for the sensor 310.

With respect to the sensor 310 depicted in FIG. 3A, the coil of sensor 310 is in the shape of a helix. The dimensions of the helix (i.e., the length L, the distance d between two adjacent loops, and a diameter D of the helix, as shown in FIG. 3A) may be chosen to create an optimum sensor 310. A pitch angle α may be used to define the helix and be calculated by:

$$\alpha = \tan^{-1}\left(\frac{d}{\pi D}\right).$$

The pitch angle α indicates the density of loops of the printed helix along the longitudinal axis of the instrument 300.

In embodiments, the sensor 310 may include multiple layers. Specifically, after a conductive material is applied to the instrument 300 to form a first coil of sensor 310, a non-conductive material may be applied over the first coil, and the second coil formed of a conductive material may be applied over both the non-conductive material and the first coil on the instrument 300. This may continue until a desired number of coils are fabricated or printed on the instrument 300. Each coil may have a different configuration, e.g., a different orientation, a different length L, and a different distance d between two adjacent loops of a helix from that of the other coils. Alternatively, each of the multiple coils of the sensor 310 may be applied to different locations of the instrument 300. In embodiments, each coil may be substantially orthogonal to each other.

In an aspect of the present disclosure, the rotational direction of the helix of one coil may be different from that of another coil. That is, one helix may have the counter clockwise orientation and another one may have the clockwise orientation. In another aspect, the conductive material may be copper, silver, gold, conductive alloys, or conductive polymer, and the non-conductive material may be ETFE, PTFE, non-conductive polymer, or polyimide.

According to a further aspect of the present disclosure, each of the end portions of the helix 310 may have a larger area for electrical contacts 320 and 330 than other areas of conductive material in the helix. Wires are connected to each of the contacts 320 and 330. These wires may extend the length of the catheter assembly 100 and be connected to the tracking device 160. As described in more detail below, in another embodiment, the wires are integrated into the instrument 300 by printing conductive material directly on to the instrument 300 to couple the sensor 310 to the tracking device 160. Thus, when the instrument 300 is located within an electromagnetic field, electrical signal (e.g., voltage) may be induced in the sensor 310 while the instrument 300 is moving inside the electromagnetic field. The induced electrical signal is transmitted to the tracking device 160, which calculates a location of the instrument 300 with respect to a coordinate system of the electromagnetic field. This calculated location may be registered to the 3D model so that a computing device may display the location in the 3D model on a display. In this way, the clinician may identify the relative location of the instrument 300 in the 3D model and 2D images of the navigation and procedure software as described above.

The induced voltage is derived from the Maxwell's equations and is calculated by the following equation:

$$\varepsilon_{ind} = -N\frac{\Delta\Phi}{\Delta t},$$

where $\varepsilon_{ind}$ is the induced voltage, N is the number of loops in the helix, ΔΦ is the change of magnetic flux of the electromagnetic field, and Δt is the change in time. The magnetic flux Φ is a product of the magnitude of the magnetic field and an area. In the same way, the change of magnetic flux, ΔΦ, is a product of the change of the magnitude of the magnetic field and the area of the one loop in the helix. Thus, the more loops in the helix, the larger the magnitude of the induced voltage is. And the faster the change of the magnetic flux, the higher the magnitude of the induced voltage is. The negative sign indicates that the induced voltage is created to oppose the change of the magnetic flux.

Since the instrument 300 is typically moved slowly and with some caution inside of the body or in a luminal network of an internal organ and the size of the loops in the helix is to be minimal, the number of loops in the helix may be sufficiently large to compensate the slow movements and the size of the loops in order to have a recognizable induced electrical signal. Thus, when a sensitivity level of the induced electrical signal and a magnitude level of the electromagnetic field are determined, the number of loops in the coil sensor 310 may be determined by the following:

$$N = -\frac{\varepsilon_{ind}\Delta t}{\Delta\Phi}.$$

The sensor 310 may sense different EM fields generated by the EM field generating device 145, in one embodiment employing three coils in the sensor 310 three separate fields are sensed. The strength of the EM field decreases proportionally with the reciprocal of the square of the distance from the source (e.g., the EM field generating device 145). Thus, the magnitude of the voltage induced by an EM field includes information defining the distance of the sensor 310 from the EM field generating device 145. By determining the distance information based on the induced electrical signal, a location of the sensor 310 can be identified with respect to the location of the EM field generating device 145.

In an aspect, where the EM field generating device 145 generates three EM fields, which may have three different directivity patterns such as x-, y-, and z-axes, respectively, induced electrical signal may have different patterns when the instrument 300 having the sensor 310 moves in any direction within the coordinate system of the EM fields. For example, when the instrument 300 moves in the x-axis direction, strengths of EM fields having y- and z-axes directivity patterns will display larger differences as compared to the sensed changes in strength of the EM field having x-axis directivity. Thus, the location of the instrument 300 may be identified by checking patterns of induced voltage sensed by the sensor 310.

In accordance with the present disclosure, sensor 310 may be printed directly onto the instrument 300. That is, during the manufacture of the instrument 300, one of the processing steps is to apply one or more conductive inks or other materials to the instrument 300. This printing may be performed by a number of processes including ink jet printing, flexographic printing, vapor deposition, etching, and others known to those of skill in the art without departing from the scope of the present disclosure.

Figure 4:
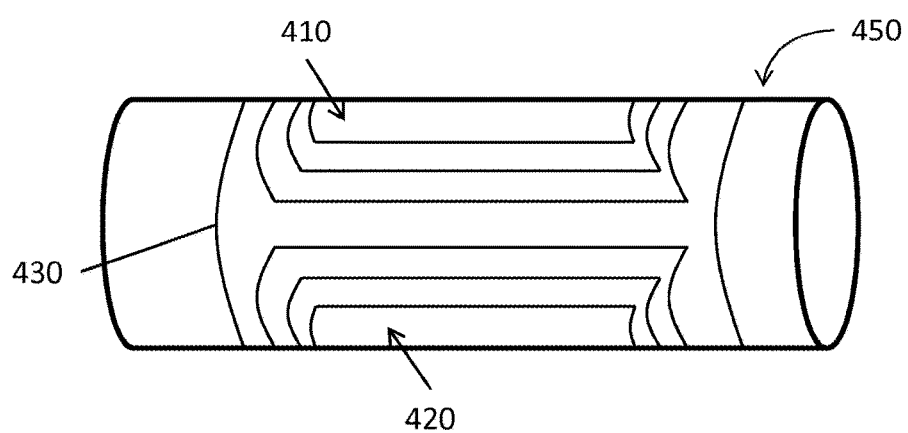
FIG. 4 is an expanded view of a distal portion of a medical instrument around which a circuit is printed in accordance with an embodiment of the present disclosure.

FIG. 4 shows sensors 410, 420 printed on a surface of an instrument 450, such as a medical instrument. The sensor 400 may have a thickness of about 0.01 to 0.05 millimeter (mm) so that the sensor can be printed on an instrument without appreciably increasing its dimensions. In accordance with one embodiment, a conductive material 415 is printed directly onto the instrument 300, to form a coil 410 or 420 and a second non-conductive film 430 covers the conductive material. Thus, the coil 410 or 420 is protected by the non-conductive film 430.

As described above, in one aspect of the present disclosure, each coil may have a different rotational orientation. The first coil 410 may have the clockwise rotational orientation and the second coil 420 may have the counter clockwise rotational orientation. Nevertheless, when the sensor 400 is printed directly on the instrument 450 so that two coils are facing each other across the longitudinal axis of the tube, the first and second coils 410 and 420 may have the same rotational orientation.

Figure 5:
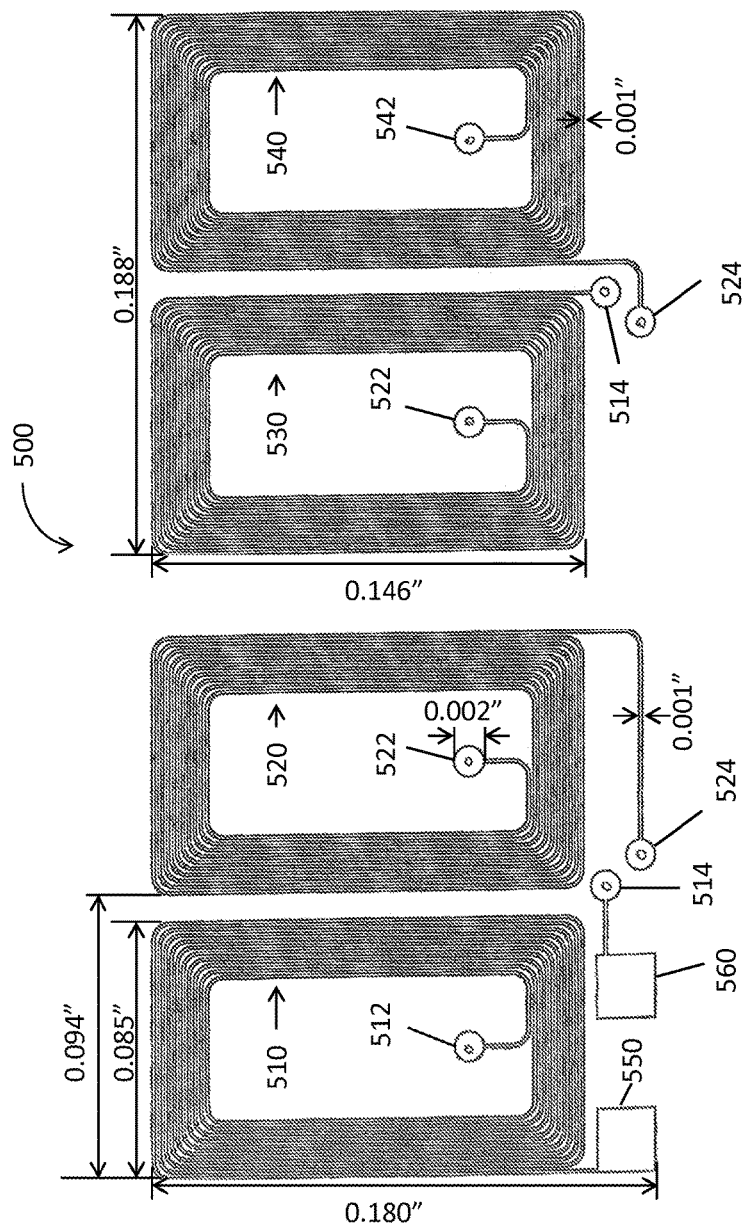
FIG. 5 is an illustrative design of a sensor including two-coils in a multi-layer circuit in accordance with an embodiment of the present disclosure.

FIG. 5 shows a double layered circuit sensor 500 in accordance with embodiments of the present disclosure. Although not depicted, it is imagined that the double layered circuit sensor 500 is printed directly on an instrument. The double layered circuit sensor 500 includes a first coil 510, a second coil 520, a third coil 530, and a fourth coil 540. The top layer includes the first and second coils 510 and 520 and the bottom layer includes the third and fourth coils 530 and 540. The double layered circuit sensor 500 further includes first and second contacts 550 and 560, and first, second, third, and fourth vias 512, 514, 522, and 524.

In one non-limiting example of the present disclosure the conductive material of each loop of any of the coils 510-540 may be approximately 9 microns thick. The thickness of the conductive material may vary based on the specifications of the circuit sensor 500, and can be larger or smaller than 9 microns for a particular application without departing from the scope of the present disclosure. In accordance with one embodiment of the present disclosure, each loop of the coils 510-540 of the top and bottom layers, respectively may be separated from each other by approximately 0.009 inches. The length and the width of the outermost loop of each coil may be approximately 0.146 inches and approximately 0.085 inches, respectively. The width of the conductive material may be approximately 0.001 inch or from about 0.025 to 0.5 mm. The vias may have a diameter of approximately 0.002 inches. The thickness of the circuit sensor 500 may be approximately 0.005 inches or from about 0.01 to 0.15 mm. The length and the width of the circuit sensor 500 may be approximately 0.180 and approximately 0.188 inches, respectively. The gap between closest loops of the same coil may be typically about 0.0005 inch.

As depicted in FIG. 5, the first contact 550 is connected to one end of the first coil 510 and the first via 512 is connected to the other end of the first coil 510. The first via 512 connects the first coil 510 of the top layer to one end of the fourth coil 540 of the bottom layer. The other end of the fourth coil 540 is connected to one end of the second coil 520 of the top layer through the fourth via 524. The other end of the second coil 520 is connected to one end of the third coil 530 of the bottom layer through the third via 522. The other end of the third coil 530 is connected to the contact 560 on the top layer through the second via 514. In this way, the four coils 510, 520, 530, and 540 are all connected to the first and second contacts 550 and 560, forming one sensor with the four coils connected electrically in series. Since the four coils are all connected to each other, and the number of loops in one sensor is the sum of the loops of the four coils 510, 520, 530, and 540, the result is an increase in sensitivity of the electromagnetic field.

According to a further aspect of the disclosure, the first and second coils 510 and 520 may have different rotational orientations and, likewise, the third and fourth coils 530 and 540 may have different rotational orientations. That is, if the first coil 510 has the counter clockwise orientation, the second coil 520 has the clockwise orientation. In the same way, if the third coil 530 has the counter clockwise orientation, the fourth coil 540 has the clockwise orientation. In another aspect, the first and fourth coils 510 and 540 may have the same rotational orientation and the second and third coils 520 and 530 may have the same rotational orientation.

As shown in FIG. 5, the first and second contacts 550 and 560 are made larger than the width of each loop of the coils. Generally, each coil of the circuit sensor 500 is coated by a non-conductive material. In an aspect, the first and second contacts 550 and 560 may not be covered by the non-conductive material so that the multi-layered circuit sensor 500 may be easily connected to wires which transmit the induced electrical signal (e.g., voltage and/or current) to an external apparatus, such as the tracking device 160 for incorporation into and use with the navigation and procedure software described above.

Figure 6A:
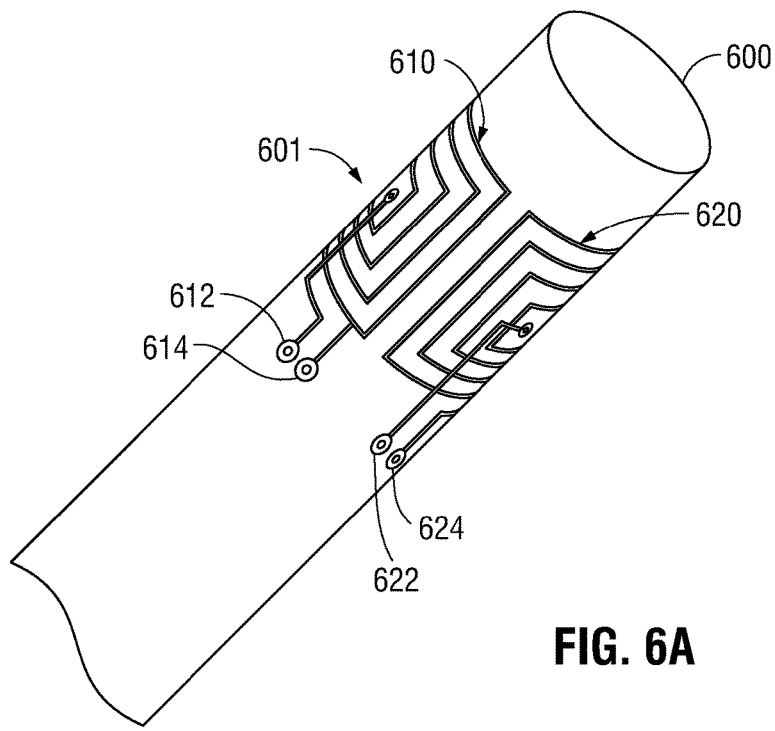
FIG. 6A is an illustrative design of two sensors in a first layer of a multi-layer circuit in accordance with an embodiment of the present disclosure.
Figure 6B:
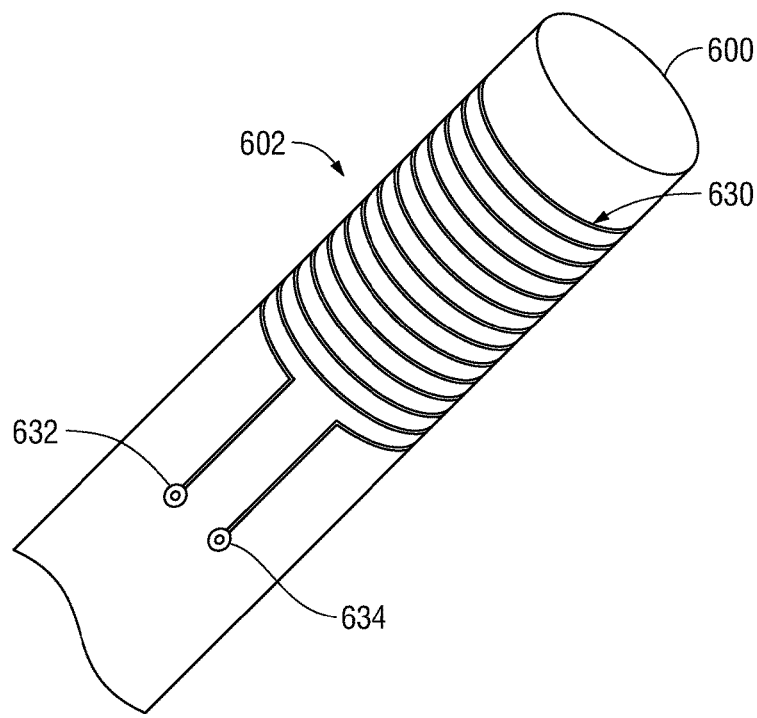
FIG. 6B is an illustrative design of a sensor in a second layer of a multi-layer circuit in accordance with an embodiment of the present disclosure.
Figure 6C:
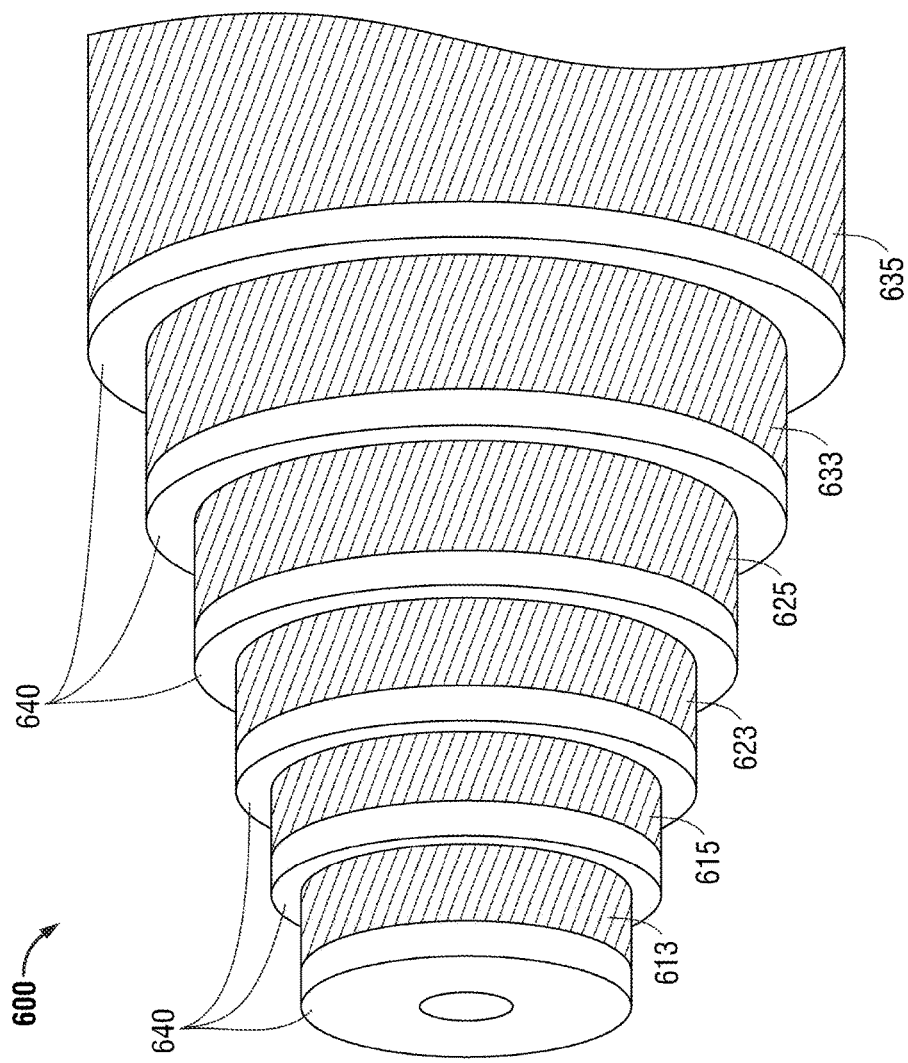
FIG. 6C is an illustrative design of a proximal portion of a medical instrument around which a series of conductive and nonconductive layers are printed.

FIGS. 6A-6C show an exemplary embodiment of a multi-layered circuit sensor printed directly on an instrument or EWC 600. FIGS. 6A and 6B show a first and second layered printed circuit sensor 601, 602. Each layer can contain one or more printed sensors. FIG. 6C shows the different layers of the EWC 600. As depicted in FIG. 6A, the first layer contains first and second sensors 610, 620 and the second layer (shown in FIG. 6B) contains a third sensor 630. Although shown separately, it is imagined that the second layer (shown in FIG. 6B) is printed on top of the first layer (shown in FIG. 6A). For convenience purpose only, loops of each coil are illustrated in FIGS. 6A and 6B in a simplified schematic fashion to only a couple of loops, however, each loop in FIG. 6 may represent more than one loop, and the number of loops may be more in line with those of coils 510-540 of FIG. 5. The sensors 610, 620, 630 are printed on a distal portion of EWC 600. FIG. 6C shows different conductive and nonconductive layers printed on a proximal portion of EWC 600. The conductive and nonconductive layers are coupled to the ends of first, second, and third sensors 610, 620, 630 by the terminals or vias 612, 614, 622, 624, 632, 634 and electrically couple the sensors to the tracking device 160.

As previously mentioned, sensors 610, 620, 630 are printed in layers. In particular, the first layer, containing the first and second sensors 610, 620, is printed directly on a nonconductive layer of the EWC 600. A second nonconductive layer is then printed on top of the first and second sensors 610, 620. The second layer, containing the third sensor 630, is then printed on top of the second nonconductive layer. This process may continue until a desired number of sensors are printed on the EWC 600. In one aspect, the final layer is a nonconductive layer. In yet another aspect, the conductive material may be copper, silver, gold, conductive alloys, or conductive polymer, and the non-conductive material may be Kapton, ETFE, PTFE, non-conductive polymer, or polyimide. Each sensor may have a different configuration or orientation, e.g., a different length L and a different distance d between two adjacent loops of a helix from that of the other coils.

As depicted in FIGS. 6A and 6B, each sensor 610, 620, 630 contains a via 612, 614, 622, 624, 632, 634 connected to the terminals of each sensor 610, 620, 630. In particular, sensor 610 contains first and second vias 612, 614, sensor 620 contains third and fourth vias 622, 624, and sensor 630 contains vias 632, 634. In embodiments, each via is electrically coupled to a different conductive layer on the proximal portion of the EWC 600, as shown in more detail in FIG. 6C.

FIG. 6C depicts an embodiment of an EWC 600 and the various layers of conductive and nonconductive material printed directly onto the instrument. FIG. 6C is not drawn to scale and is meant for illustrative purposes only. Each layer of conductive and nonconductive material may range in thickness from 9 microns to 0.05 millimeters (mm).

EWC 600 comprises a hollow tube consisting of an inner Teflon liner, e.g. PTFE. The Teflon liner provides lubricity for easy sliding of tools down the center of the EWC 600. In one embodiment, the first, second, and third sensors 610, 620, 630 are printed directly on the Teflon layer. Above the Teflon layer is a wire braid layer (not shown). The wire braid helps provide structural integrity and torquability to allow for easy maneuverability of the EWC 600. The final layer is a thermal plastic layer which, through a heat process, bonds all three layers together to provide durability.

As described above, the first, second, and third sensors 610, 620, 630 are printed on the distal portion of EWC 600 on the Teflon layer. On the proximal portion of the EWC 600, nonconductive layers 640 and conductive layers 613, 615, 623, 625, 633, 635 are printed directly on the Teflon layer in layers in alternating fashion. In other words, a base nonconductive layer 640 is printed on top of the Teflon layer followed by a conductive layer 613 printed on top of the base nonconductive layer. Another nonconductive layer is then printed on top of conductive layer 613 and another conductive layer 615 is printed on top of the nonconductive layer. This process is then repeated until a desired number of nonconductive and conductive layers are achieved. In embodiments, the final layer is a nonconductive layer. The wire braid and thermal plastic layer are then placed on top of the final nonconductive layer. The embodiment shown in FIG. 6C illustrates a total of six conductive layers 613, 615, 623, 625, 633, 635 and seven nonconductive layers 640. In aspects, the conductive material may be copper, silver, gold, conductive alloys, or conductive polymer, and the nonconductive material may be Kapton, ETFE, PTFE, nonconductive polymer, or polyimide.

The conductive layers function as wires and form a return path for sensors 610, 620, 630, connecting the sensors to tracking device 160. For example, in one embodiment, the conductive layer 613 is coupled to via 612, conductive layer 615 is connected to via 614, conductive layer 623 is connected to via 622, conductive layer 625 is connected to via 624, conductive layer 633 is connected to via 632, and conductive layer 635 is connected to via 634.

Since the sensors 610, 620, 630 are very thin, the sensors 610, 620, 630 have a high resistance, however, a low resistance is desired for the return path. In one embodiment, each conductive layer 613, 615, 623, 625, 633, 635 is printed 360 degrees around the EWC 600 and along the length of EWC 600 back to the proximal end in order to reduce the resistance on the return path.

The measured resistivity of the sensors 610, 620, 630 and the conductive layers 613, 615, 623, 625, 633, 635 is a function of a number of factors including the length, width, and thickness of the conductive material as well as the resistive properties of the conductive material used. In one experiment, a sensor made up of 200 turns of a conductive material having a resistance of $1.68 \times 10^{-5}$ Ωmm and printed around the distal end of EWC 600, having a length of 1256 mm, a width of 0.47 mm, and a thickness of 0.01 mm measured a total resistance of 179.58Ω. Likewise, a sensor made up of 300 turns, having a length of 1884 mm, and a thickness of 0.015 mm measured a total resistance of 269.37Ω. In experiments, a return path made up of the same conductive material printed along the length of an EWC 600 having a length of 1020 mm and circumference of 6.28 mm measured a resistance of 10.92Ω. The low resistivity of the conductive return paths helps to lower the amount of noise in the signal from the sensors 610, 620, 630 back to the tracking device 160.

Figure 7:
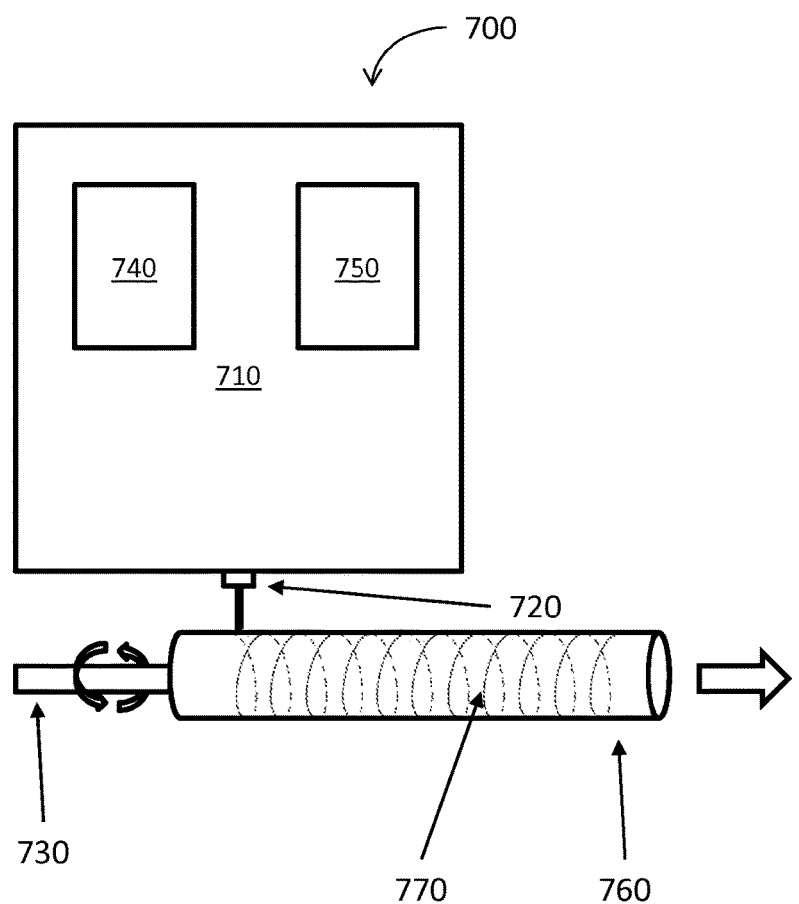
FIG. 7 is an illustration of a printer that prints a sensor on a surface of a medical instrument in accordance with an embodiment of the present disclosure.

As described above, one methodology for applying sensors to instruments is via printing directly on the instruments. FIG. 7 shows a printing apparatus 700 that prints conductive and non-conductive materials directly to the desired locations of the instruments. The printing apparatus 700 includes a reservoir 710, a printing nozzle 720, and an actuating arm 730. The reservoir 710 includes a first tank 740, which contains a conductive material, and a second tank 750, which contains a non-conductive material. The printing apparatus 700 can print a circuit on any instruments 760, which can be locked into the distal end of the actuating arm 730. In an aspect, the printing apparatus may print a sensor over a polymer.

A controller of the printing apparatus 700, which is not shown in FIG. 7, controls an actuating motor, which is not shown in FIG. 7, to move the actuating arm 730. The actuating motor is fixedly connected to the proximal end of the actuating arm 730. The actuating motor can index forward and backward and rotate the actuating arm 730. In an aspect, the actuating motor may move the reservoir 710 while printing. In another aspect, the actuating motor may move the reservoir 710 and the actuating arm 730 simultaneously. For example, the actuating motor may index forward or backward the reservoir 710 while rotating the actuating arm 730. Still further, the reservoir 710 and instrument 760 may be held motionless while the printing nozzle 720, which is fluidly connected to the reservoir 710, moves about the instrument 760. Further, combinations of these techniques may be employed by those of skill in the art without departing from the scope of the present disclosure.

In one embodiment, with the proximal end of an instrument 760 locked into the distal end of the actuating arm 730, the printing nozzle 720 may start printing the conductive material contained in the first tank 740 while the actuating arm 730 is moved forward and rotated by the actuating motor. Velocities of indexing and rotating are controlled to print a helix-type sensor 770 on the instrument 760. When the velocity of indexing is faster than the velocity of rotating, the helix-type sensor 770 will have a large pitch angle or have loose loops in the helix. On the other hand, when the velocity of indexing (indexing velocity) is slower than the velocity of rotating (angular velocity), the helix-type sensor 770 will have a small pitch angle or have dense loops in the helix. Relationship between the pitch angle and velocities is shown below as follows:

$$\alpha = \tan^{-1}\left(\frac{v_i}{Dv_\theta}\right),$$

where α is the pitch angle, $v_i$ is the indexing velocity, $v_\theta$ is the angular velocity of rotation in radian, and D is the cross-sectional diameter of the instrument 760. Thus, the controller may control the indexing velocity $v_i$ and the angular velocity $v_\theta$ so that the printed circuit 770 can have a pitch angle suitable for its purpose.

In an aspect, the printing may be started from the distal end of the instrument 760 or the proximal end of the instrument 760. In a case when the printing is started from the distal end of the instrument 760, the actuating arm 730 indexes the instrument 760 forward so that the printing nozzle 720 can print the conductive material toward the proximal end of the instrument 760. In another case when the printing is started from the proximal end of the toll 760, the actuating arm 730 indexes the instrument 760 backward so that the printing nozzle 720 can print the conductive material toward the distal end of the instrument 760. In another aspect, the actuating arm 730 may change the direction of rotation so that the helix-type sensor 770 can have the counter clockwise or clockwise helix.

The printing nozzle 720 may print more conductive material in the beginning and end of the printing so that each end of the helix-type sensor 770 has a larger area for contact to an external apparatus. In another aspect, after one layer of the helix-type sensor 770 is printed, the actuating arm 730 may perform a reverse indexing and rotating motion, meaning that indexing backward is performed when indexing forward is performed while the helix-type sensor 770 is printed and that counter clockwise rotation is performed when clockwise rotation is performed while the helix-type sensor 770 is printed. At the same time, the printing nozzle 720 may print the non-conductive material over the printed conductive material. In this way, the printed conductive material may be wholly covered by the non-conductive material. The printing nozzle 720 may be controlled to print the non-conductive material over a larger area than an area of the printed conductive material. This may give more certainty that the printed conductive material is completely covered by the non-conductive material.

After completion of printing the non-conductive material, the printing nozzle 720 may print the conductive material over the instrument 760 again. In an aspect, a new indexing velocity $v_i'$ and a new angular velocity $v_\theta'$ different from the original indexing velocity $v_i$ and the angular velocity $v_\theta$ may be selected so that new helix-type sensor may have different configuration from that of the original helix-type sensor. By repeating these steps, the instrument 760 may have several helix-type sensors.

In yet another aspect, the actuating arm 730 may control indexing forward and backward and rotation motions so that sensor may have different configurations. For example, the sensor may have a series of incomplete circles. This pattern can be obtained by rotating the actuating arm without indexing forward and by indexing forward it without rotation before completing a whole circle. The scope of the present disclosure may extend to similar or different configurations which may be readily appreciated by a person having ordinary skill in the art.

Figure 8:
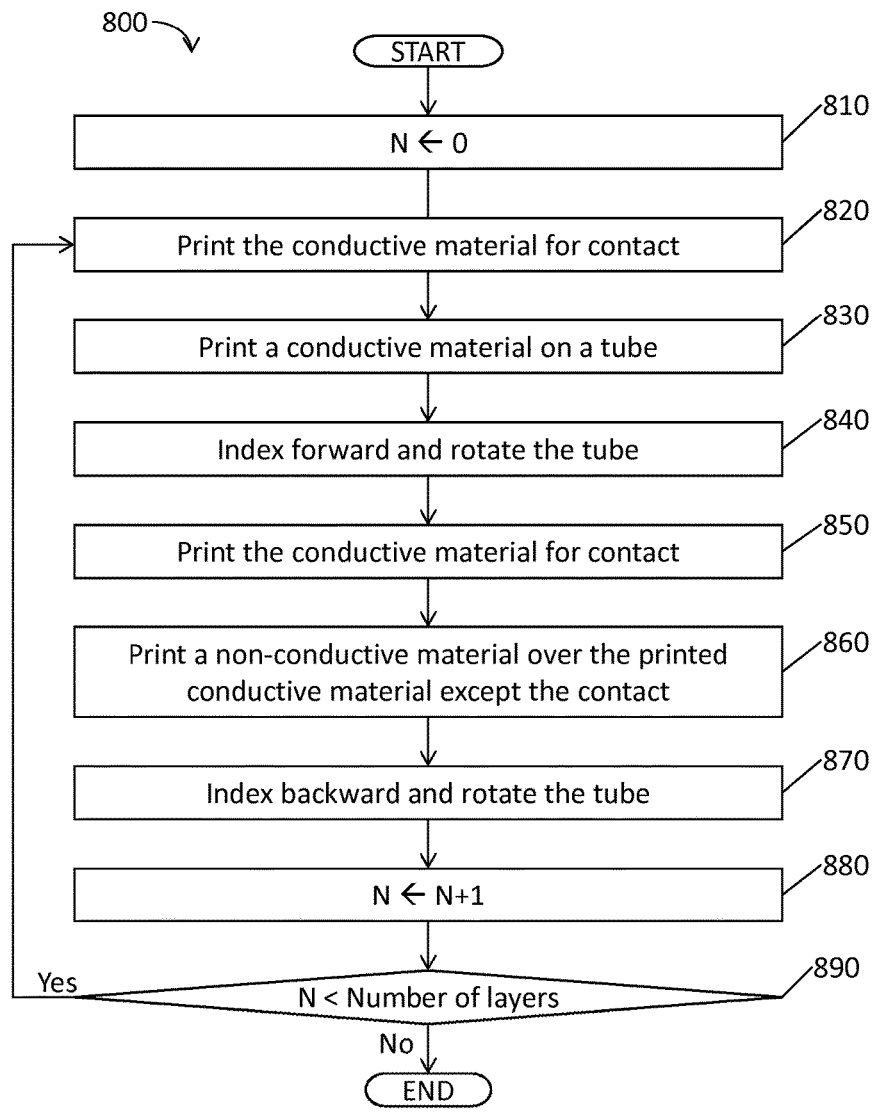
FIG. 8 is a flowchart of a method for printing a sensor on a medical instrument in accordance with an embodiment of the present disclosure.

FIG. 8 shows a method 800 of printing a sensor on a surface using a printer. The sensor may be one layered or multiple layered. The method 800 starts from setting a counter N as zero in step 810. In step 820, the printer prints the conductive material for contact to an external apparatus. The contact area may be a larger than an area for printed conductive material of the sensor. In step 830, the printer prints a conductive material on the tube. While printing, in step 840, an indexing arm of the printer, which holds the tube, indexes forward or backward, and rotates the tube. Here, an indexing velocity and an angular velocity of the indexing arm may be controlled to make a specific pattern of the sensor as described above in FIG. 7.

In step 850, the printer prints the conductive material for another contact. The contacts printed in steps 810 and 850 are to be used to connect to wires which lead to and connect with an external apparatus such as the tracking device 160 of FIG. 1. The tracking device can process the sensed results to identify the location of the sensor in an electromagnetic field, as described above.

In step 860, the printer prints a non-conductive material to form a non-conductive film over the printed conductive material. While printing the non-conductive material, in step 870, the actuating arm of the printer indexes forward or backward and rotates in a direction reverse from the direction of printing the conductive material. In this way, the printed conductive material is insulated from or protected from other environments. This step concludes the printing of the sensor.

In step 880, the counter N is incremented by one. In step 890, the counter N is compared with a predetermined number of layers. If the counter N is less than the predetermined number of layers, the method 800 repeats steps 820 through 890. If the counter N is not less than the predetermined number of layers, the method is ended.

In an aspect, when the predetermined number of layers is greater than 1, a sensor printed in each layer may have different configuration, such as a helix pattern as shown in FIG. 7 and a pitch angle. Alternatively, the sensors in a multiple layers may be all connected so that the sensors only have two contacts rather than a sensor in each layer has two contacts separate from two contacts of another sensor.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. A medical instrument, comprising:
    a base non-conductive layer on a distal portion of the medical instrument;
    a sensor printed on the base non-conductive layer, the sensor including a first conductive coil, a second conductive coil, and a non-conductive layer disposed between the first conductive coil and the second conductive coil;
    a proximal conductive layer printed circumferentially around a proximal portion of the medical instrument;
    a proximal non-conductive layer printed on the proximal conductive layer; and
    at least one pair of contacts electrically connected to at least one of the first conductive coil or the second conductive coil of the sensor and coupled to the proximal conductive layer, the proximal conductive layer connectable to a measurement device configured to sense an induced electrical signal in the sensor based on a magnetic flux change of an electromagnetic field,
    wherein a location of the medical instrument in a coordinate system of the electromagnetic field is identified based on the induced electrical signal in the sensor.

2. The medical instrument according to claim 1, wherein each of the first conductive coil and the second conductive coil includes a conductive layer formed of a conductive material, the conductive layer of the first conductive coil having a different configuration from a configuration of the conductive layer of the second conductive coil.

3. The medical instrument according to claim 2, wherein the different configuration includes a pitch angle and a number of loops of the conductive material.

4. The medical instrument according to claim 1, wherein the proximal portion of the medical instrument includes a plurality of proximal conductive layers and proximal non-conductive layers printed on the proximal portion of the medical instrument.

5. The medical instrument according to claim 4, wherein each proximal conductive layer of the plurality of proximal conductive layers is coupled to at least one of the first conductive coil or the second conductive coil of the sensor.

6. The medical instrument according to claim 1, wherein at least one of the first conductive coil or the second conductive coil of the sensor is connected to the proximal conductive layer through vias.

7. The medical instrument according to claim 1, wherein at least one of the first conductive coil or the second conductive coil of the sensor forms a helical shape.

8. The medical instrument according to claim 7, wherein the helical shape is counter clockwise.

9. The medical instrument according to claim 7, wherein the helical shape is clockwise.

10. The medical instrument according to claim 1, wherein an outer surface of the medical instrument is made of ETFE, PTFE, polyimide, or non-conductive polymer.

11. The medical instrument according to claim 1, wherein at least one of the first conductive coil or the second conductive coil of the sensor includes copper, silver, gold, conductive alloys, or conductive polymer.

12. The medical instrument according to claim 1, wherein the medical instrument is an extended working channel, an imaging instrument, a biopsy forceps, a biopsy brush, a biopsy needle, or a microwave ablation probe.

13. A sensor, comprising:
a first conductive coil positioned at a distal portion of a medical instrument;
a non-conductive layer positioned on at least a portion of the first conductive coil at the distal portion of the medical instrument; and
a second conductive coil positioned on at least a portion of the non-conductive layer at the distal portion of the medical instrument,
wherein the first conductive coil is spaced apart from the second conductive coil along a direction orthogonal to a surface of the non-conductive layer facing the first conductive coil.

14. The sensor according to claim 13, wherein the first conductive coil overlaps the second conductive coil along the direction orthogonal to the surface of the non-conductive layer facing the first conductive coil.

15. The sensor according to claim 13, wherein the first conductive coil is positioned on a non-conductive base layer of the medical instrument.

16. A medical instrument, comprising:
a sensor positioned at a distal portion of the medical instrument, the sensor comprising:
a first conductive coil positioned at the distal portion of the medical instrument;
a non-conductive layer positioned on at least a portion of the first conductive coil; and
a second conductive coil positioned on at least a portion of the non-conductive layer; and
a tracking device configured to sense an induced electrical signal in the sensor based on a variation of an electromagnetic field,
wherein a location of the sensor in a coordinate system of the electromagnetic field is configured to be determined by the tracking device based on the induced electrical signal in the sensor.

17. The medical instrument according to claim 16, wherein the first conductive coil overlaps the second conductive coil along a direction orthogonal to a surface of the non-conductive layer facing the first conductive coil.

18. The medical instrument according to claim 16, wherein the first conductive coil is positioned on a non-conductive base layer of the medical instrument.

19. The medical instrument according to claim 16, wherein the first conductive coil includes copper, silver, gold, a conductive alloy, or a conductive polymer.

20. The medical instrument according to claim 16, wherein the medical instrument is an extended working channel, an imaging instrument, a biopsy forceps, a biopsy brush, a biopsy needle, or a microwave ablation probe.

* * * * *